United States Patent [19]

Baumberg

[11] Patent Number: 4,722,349

[45] Date of Patent: Feb. 2, 1988

[54] ARRANGEMENT FOR AND METHOD OF TELE-EXAMINATION OF PATIENTS

[75] Inventor: Iosif Baumberg, Brooklyn, N.Y.

[73] Assignee: Zvi Halperin, Montreal, Canada

[21] Appl. No.: 537,262

[22] Filed: Sep. 29, 1983

[51] Int. Cl.⁴ .............................................. A61B 5/02
[52] U.S. Cl. .................................... 128/681; 128/677; 128/904
[58] Field of Search ............... 128/672, 677, 680–683, 128/904

[56] References Cited

U.S. PATENT DOCUMENTS

| | | | |
|---|---|---|---|
| 2,827,040 | 3/1958 | Gilford | 128/681 |
| 3,654,915 | 4/1972 | Sanctuary | 128/682 |
| 3,742,938 | 7/1973 | Stern | 128/904 X |
| 4,068,096 | 1/1978 | Rattenborg et al. | 128/904 X |
| 4,116,230 | 9/1978 | Gorelick | 128/682 |
| 4,216,779 | 8/1980 | Squires et al. | 128/682 |
| 4,319,241 | 3/1982 | Mount | 128/904 X |
| 4,325,383 | 4/1982 | Lacks | 128/677 |
| 4,326,536 | 4/1982 | Kitagawa et al. | 128/682 |
| 4,367,751 | 1/1983 | Link et al. | 128/681 X |
| 4,461,266 | 7/1984 | Hood, Jr. et al. | 128/680 X |
| 4,539,997 | 9/1985 | Wesseling et al. | 128/681 X |
| 4,576,178 | 3/1986 | Johnson | 128/670 |

*Primary Examiner*—William E. Kamm
*Assistant Examiner*—Angela D. Sykes
*Attorney, Agent, or Firm*—Ilya Zborovsky

[57] ABSTRACT

A tele-examination of patients' pulse and blood pressure is performed by automatically measuring the pulse and blood pressure and transmitting electrical impulses of sound impulses corresponding thereto without time or frequency separation via communicating channel, such as a telephone.

5 Claims, 2 Drawing Figures

ARRANGEMENT FOR AND METHOD OF TELE-EXAMINATION OF PATIENTS

BACKGROUND OF THE INVENTION

The present invention relates to an arrangement for and a method of telephone examination of patients (or other telecommunication examination) in the sense of remote receipt of information about pulse and blood pressure of patients.

Arrangements for automatic measurement of upper and lower blood pressure are known in the art. The known arrangement includes a unit of automatic inflation of an elastic inflatable sleeve, a sensor of air pressure in the sleeve, a converter of an analogous value into a discrete value, and a sensor of pulse beats. This device is not however designed for transmitting the measured values of pulse and blood pressure remotely to a physician. This would be very advisable, since with such a transmission it would be possible to examine a patient remotely without physically visiting a physician. As a result, time and labor of both the patient and the physician would be considerably economized. The same is true with respect to subsequent examination of patients over a period of time.

SUMMARY OF THE INVENTION

Accordingly, it is an object of the present invention to provide an arrangement for and a method of tele-examination of patients, which avoids the disadvantages of the prior art.

More particularly, it is an object of the present invention to provide an arrangement for and a method of tele-examination, which make possible tele-transmission of information about patient's pulse and blood pressure through a telecommunication channel such as a telephone line without frequency or time separation.

In keeping with these objects and with others which will become apparent hereinafter, one feature of the present invention resides briefly stated in an arrangement for examination of patients which comprises means for measuring blood pressure and including an inflatable sleeve to be placed on a patient's forearm, means for pumping gas into said sleeve, means for converting pulse beats into electrical impulses, means connected with said blood pressure measuring means and receiving analogous signal from the latter and generating impulses proportional to a discrete value of pressure change, controlling means for controlling pumping of gas into said sleeve so that pumping is performed first in a first mode from an atmospheric pressure to lower blood pressure monotonously and so that when pressure in said sleeve reaches a value which is a multiple of the discrete value of pressure change quantizing an impulse is transmitted, and then in a second mode started by a signal formed by the first mentioned impulse and in which pumping is performed from lower to upper blood pressure values and each pulse beat is used as a permitting signal for gas pressure increase in said sleeve and when gas pressure in said sleeve reaches a value which is a multiple of the discrete value of pressure change the pumping is interrupted, wherein in said second mode impulses are transmitted upon the signal of beginning of pressure increase in said sleeve by the discrete value of pressure change quantizing coinciding with a time of pulse beat appearance, so that the impulses in said second mode simultaneously carry information about time moments of pulse beats and pressure increase in said sleeve, communicating means for transmitting said impulses, and receiving means for receiving the transmitted impulses.

The novel features of the invention are set forth in the claims. The invention itself, both as to the arrangement and method of the invention are described in a description hereinbelow, which is accompanied by the following drawing.

BRIEF DESCRIPTION OF THE DRAWING

The single FIGURE of the drawing is a schematic view showing an arrangement for tele-examination in accordance with the present invention.

DESCRIPTION OF A PREFERRED EMBODIMENT

Figure 1:
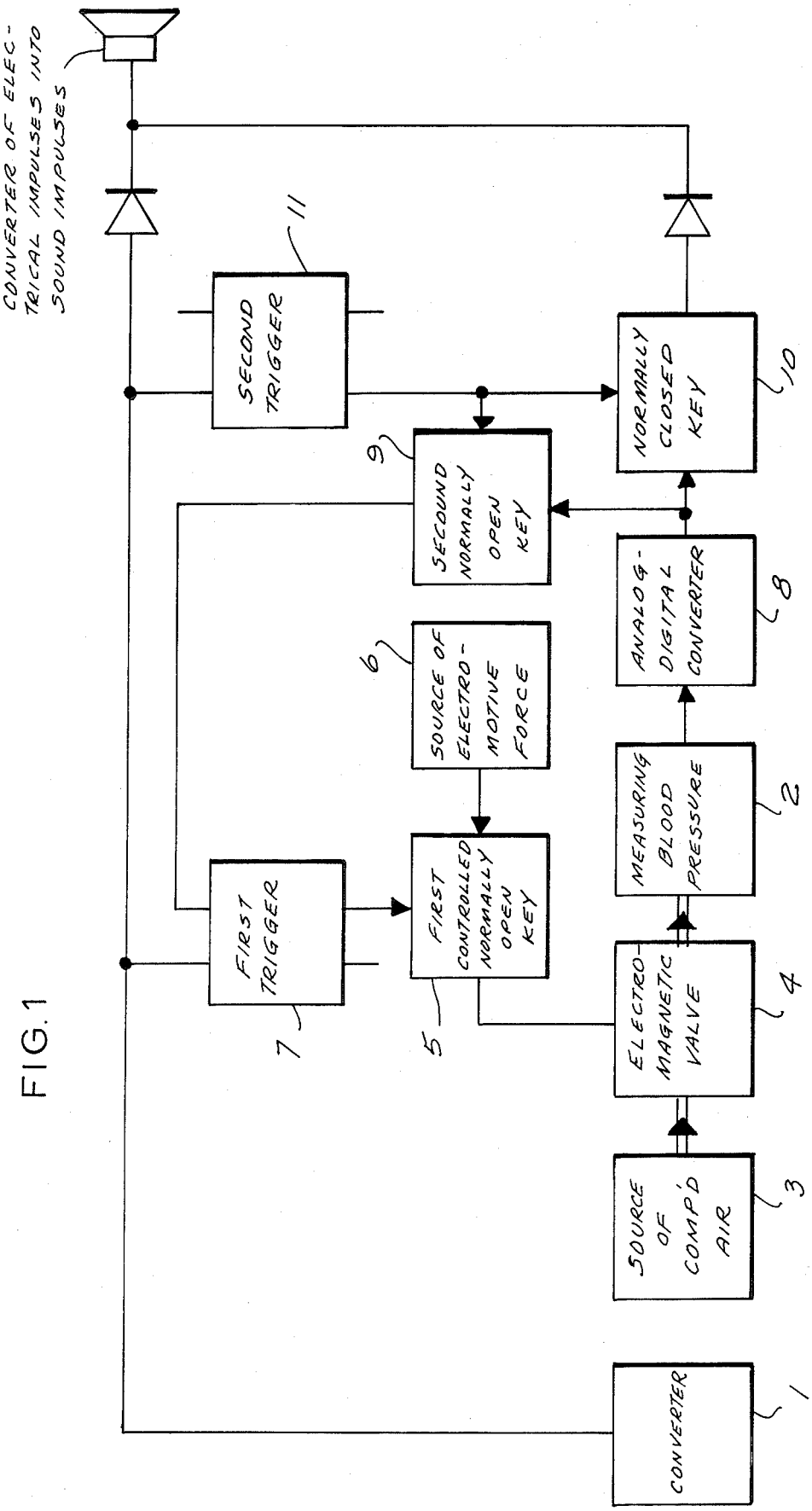
Figure 2:
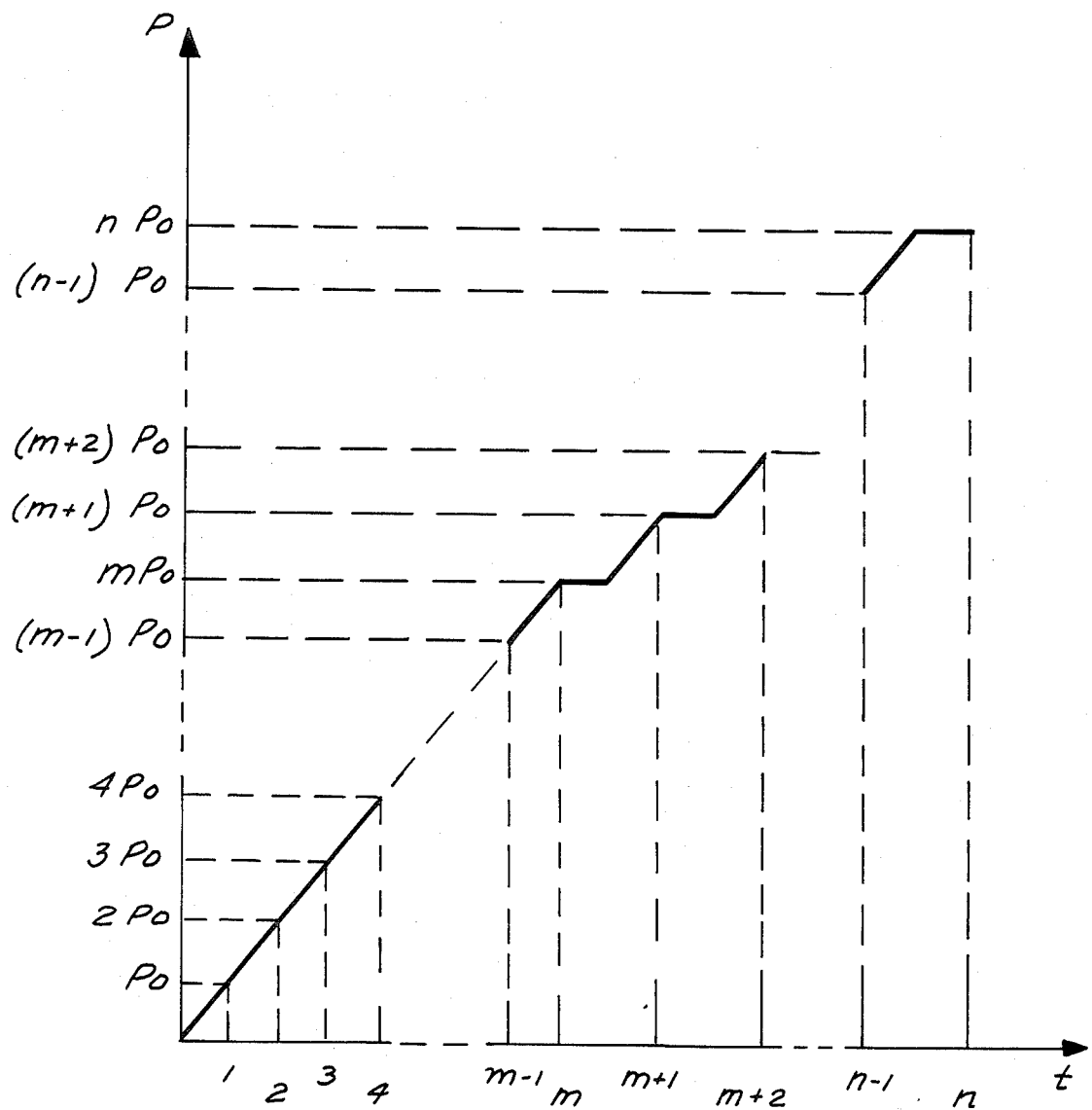

An arrangement for tele-examination of patients or a so-called doctor-phone includes a unit of measuring a pulse frequency provided with a converter for converting pulse beats into electric impulses and identified with reference numeral 1, a unit of measuring blood pressure which is identified with reference numeral 2 and has an inflatable sleeve to be placed onto a patient's forearm, and a source of compressed air 3 which automatically pumps air (gas) into the inflatable elastic sleeve of the unit 2. The above listed units are known in the art and together form an arrangement for automatic measurement of blood pressure and pulse frequency.

The arrangement in accordance with the present invention further includes a valve with an electromagnetic (solenoidal) drive identified with reference numeral 4 and arranged between the source of compressed air (gas) 3 and the inflatable sleeve of the unit 2 for measuring blood pressure, a first controlled normally open key 5 arranged in a current supply circuit between a source of electromotive force 6 and an electromagnetic (solenoidal) drive of the valve 4, a first trigger 7 with two separate inlets and wherein a second outlet of the trigger 7 is connected with a controlling inlet of the normally open key 5, an outlet of air pressure sensor in the sleeve connected with an inlet of a device (analogous-digital converter) 8 which will be explained in detail hereinbelow, a controlled second normally open key 9 and a controlled normally closed key 10 whose controlling inlets are connected with the first outlet of the second trigger 11. A first inlet of the second trigger 11 is connected with the first inlet of the first trigger 7 and also with the outlet of the converter of pulse beats into the electrical impulses 2 and with the inlet of a converter of electrical impulses into sound impulses 12. The outlet of the controlled normally closed key 10 is also connected with the converter 12, whereas the outlet of the controlled normally open key 9 is connected with the second inlet of the first trigger 7. The outlets of the converter of pulse into electrical impulses 1 and of the normally closed key 10 are connected with the inlet of the converter of electrical impulses through separating diodes into sound impulses 12. It is also possible to connect these outlets directly with a communication line without the converter 12.

Electrical impulses generated in time moments of pulse beats of a patient are supplied from the outlet of the unit 1, whereas from the outlet of the unit 2 an analogous electrical signal is supplied with an amplitude which monotonously increases as a function of air pressure value in the inflatable elastic sleeve and into the inlet of the device 8. Electrical impulses are supplied from the outlet of the device 8 so that each of the impulses is generated when gas pressure in the inflatable sleeve reaches a value P which is a multiple of a predetermined discrete value of pressure change $\Delta P$ $P=k\cdot\Delta P$ ($k=1, 2, \ldots$). The impulses from the device 8 sleeve are supplied through the normally closed key 10 and the separating diode to the inlet of the converter of the electrical impulses into the sound impulses 12 or, without passing through the converter 12, directly into a telephone communication line through a telephone apparatus.

The source of compressed air supply 3, resistance of channels connecting the source with the inflatable sleeve, and the discrete values of pressure change $\Delta P$ are selected so that the frequency of quanting of pressure value $\nu\Delta P$ is considerably greater than a possible frequency of pulse beats of a patient $\nu_0$, $\nu\Delta P > Z > > \nu_0$. The triggers with two inlets are not symmetrical, and after connecting the arrangement with a supply source they are set into positions in which there is no voltage at the second outlet of the first trigger 7 and at the first outlet of the second trigger, and the normally open keys 5 and 9 are in an open position. In this condition the supply circuit of the electromagnetic device of the valve 4 with the source of electromotive force is broken. In this case air from the pressure source 3 passes through the valve 4 into the inflatable sleeve of the unit of measuring blood pressure 2. The impulses of discrete values of pressure change however are not supplied to the second inlet of the trigger 7, but instead are supplied via the normally closed key 10 and the separating diode to the inlet of the converter of converting the electrical impulses into sound impulses 12, or directly into the line of telephone communication if the transmission does not take place via a microphone of the telephone apparatus of a patient.

When the air pressure in the inflatable sleeve reaches a value equal to the lower blood pressure of a patient, a first beat occurs which is an impulse of blood pressure, and as a result a first electrical impulse at the outlet of the unit of measuring of pulse frequency 1 takes place. Because of this, the position of the first trigger 7 does not change, whereas the second trigger 11 passes to another position in which voltage occurs at its first outlet (passes to one position), and an impulse of pulse is delivered at the inlet of the device for converting electrical impulses into sound impulses 12, or directly into the communication line through the separating diode. As a result of the impulse at the outlet of the unit of measuring of pulse frequency 1, the normally open key 9 passes to the closed position, whereas the normally closed key 10 passes to the open position. Subsequently, until disconnection of the arrangement from the power source, the position of the second trigger 11 and the controlled keys 9 and 10 does not change. The impulses of discrete values of pressure change of the pressure value of air in the inflatable sleeve will not be supplied from the outlet of the converter 8 to the inlet of the generator of sound impulses 12 or directly into the line of telephone communication. After the first beat of pulse, the impulses of discrete values of pressure change of air pressure value in the inflatable sleeve are supplied via the key 9 into the second inlet of the first trigger 7. Voltage takes place at the second outlet of the trigger 7 (it passes into "one" position), the normally open key 5 passes to conducting position, the circuit of the electromagnet (solenoid) of the valve 4 becomes connected with the source of electromotive force 6. This leads to interruption of pumping of air from the source 3 into the inflatable sleeve of the unit of measuring blood pressure. This position will continue until the occurence of a next impulse of pulse, and as a result of this an impulse will appear at the outlet of the converter 1, the trigger 7 will return to its position in which there is no voltage at its second outlet (it passes to zero position), and pumping of air into the inflatable sleeve will resume. As soon as the air pressure in the inflatable sleeve increases by the discrete value of pressure change $\Delta P$, a pulse leading to interruption of pumping of air into the sleeve will appear at the outlet of the device 8. After the air pressure in the inflatable sleeve reaches the value of upper blood pressure, generation of impulses is interrupted at the outlet of the unit of measuring of pulse frequency 1 and supply of impulses from the outlet of the arrangement terminates. The absence of impulses at the outlet of the arrangement during a time interval which is greater than a maximum possible interval between moments of time of two successive beats of pulse can be used as an information for formation of a signal about termination of a measurement session and discharge of air from the inflatable sleeve.

At a receiving station, for example in a physician's office, the impulse stream received therein is analyzed with the aid of a time analyzer. There are analyzed a number of impulses $N_1$ received before occurence of the first pulse beat and a total number of impulses received during the whole measurement session N. Products $P_1 = N_1 \cdot \Delta P$ and $P_u = N \cdot \Delta P$ are respectively values of lower blood pressure and upper blood pressure. of the patient.

It is to be emphasized that in accordance with the present invention each impulse of the impulse stream transmitted to the physician in the interval between the lower blood pressure $P_1$ and the upper blood pressure $P_u$ carries simultaneously the information about two independent values of a patient, namely a value of blood pressure as well as a frequence and rhythm of pulse. Each transmitted impulse in this interval shows an excess of the upper blood pressure above the lower blood pressure $P_u$ over $P_1$ by the discrete value of pressure change $\Delta P$. Time intervals between the impulses are equal to the respective time intervals between pulse beats of a patient. From this impulse sequence, values of time parameters of pulse can be determined by known methods, such as for example an average beat frequency, presence and characteristics of arrhythmia, etc.

Because of the double conversion of the electrical impulses into the sound impulses and the latter into the electrical impulses for transmission through the communication channel, no structural changes must be introduced into the telephone apparatus of a patient. In accordance with the present invention, the converter of the electrical impulses into sound impulses 12 is arranged together with the telephone receiver of a patient into a sound-tight case or box for reducing disturbances. The converter of electrical impulses into sound impulses 12 can be dispensed with. For this purpose instead of the telephone receiver, the outlet of the above described arrangement is connected with the telephone apparatus with the aid of a switch.

It is also to be emphasized that in accordance with the present invention the information about pulse and blood pressure is transmitted from a patient to a physician without time or frequency separation.

The invention is not limited to the details shown since various modifications and structural changes are possible without departing in any way from the spirit of the present invention.

What is desired to be protected by Letters Patent is set forth in the appended claims.

I claim:

1. An arrangement for tele-examination of patients as to their pulse and blood pressure, comprising
    means for measuring pulse frequency;
    means for measuring blood pressure and including an inflatable sleeve to be placed onto a patient's forearm;
    a compressed gas source connectable with said sleeve;
    means for pumping gas into said sleeve;
    means for converting pulse beats into electrical impulses;
    generating means connected with said blood pressure measuring means and receiving an electrical analogous signal from the latter so as to generate one impulse in response to each increase of gas pressure in said sleeve by one discrete value of pressure change;
    controlling means for controlling pumping of gas into said sleeve so that the pumping is performed first in a first mode monotonously from atmospheric pressure to lower blood pressure at which first pulse beat takes place and impulses corresponding to the discrete values of pressure change are supplied, and then a second mode started by the impulse corresponding to the first pulse beat and in which pumping is performed from lower to upper blood pressure values and each pulse heat is used as a permitting signal for gas pressure increase in said sleeve by the one discrete value of pressure change, and when gas pressure in said sleeve reaches a value which is multiple of the discrete value of pressure change the pumping is interrupted, and at the same time in said second mode the impulses of pulses are supplied, so that the impulses in the second mode simultaneously carry information about time moments of pulse beats and gas pressure increase by the discrete value of pressure change in said sleeve;
    communicating means for transmitting said impulses in said first mode and in said second mode; and
    means for receiving the thus formed and transmitted impulses at a location spaced from a patient so that at said location a lower blood pressure can be determined as a product of the number of impulses in said first mode by the discrete value of pressure change, an upper blood pressure can be determined as a product of the number of impulses in both modes by the discrete value of pressure change, and time intervals between the impulses in the second mode determine time intervals between pulse beats.

2. An arrangement as defined in claim 1, wherein said communicating means are means for transmitting the thus formed electrical impulses, said receiving means being means for receiving the thus transmitted electrical impulses.

3. An arrangement as defined in claim 1, wherein said communicating means includes a converter of the thus formed electrical impulses into sound impulses and means for transmitting the sound impulses, said receiving means including means for receiving the thus transmitted sound impulses.

4. An arrangement as defined in claim 1, wherein said controlling means includes a valve having a drive and located between said gas source and said sleeve, a first normally open key arranged in a power circuit between a source of EMF and said drive of said valve, a first trigger with two inlets and outlets in which a second outlet is connected with a controlling inlet of said normally open key, a sensor of gas pressure in said sleeve connected with said generating means, controlled second normally open key and normally closed key, a second trigger with two inlets and arranged so that controlling inlets of said second normally closed key and said normally open key are connected with a first outlet of said second trigger and a first inlet of said second trigger is connected with the first inlet of said first trigger and with an inlet of said means for converting pulse beats into electrical impulses, the first inlet of said second trigger and the outlet of the normally open key being connected with said communicating means, outlet of said means for converting pulse beats into electrical impulses being also connected with said communicating means.

5. A method of tele-examination of patients as to their pulse and blood pressure, comprising the steps of
    measuring a pulse frequency;
    measuring blood pressure by blood pressure measuring means including an inflatable sleeve to be placed onto a patient's forearm;
    pumping gas from a compressed gas source into said sleeve;
    converting pulse beats into electrical impulses;
    receiving an electrical analogous signal from the blood pressure measuring means and generating one impulse in response to each increase of gas pressure in said sleeve by one discrete value of pressure change;
    controlling pumping of gas into the sleeve so that the pumping is performed first in a first mode monotonously from atmospheric pressure to lower blood pressure at which first pulse beat takes place and impulses of discrete values of pressure change are supplied, and then in a second mode started by the impulse corresponding to the first pulse beat and in which pumping is performed from lower to upper blood pressure values and each pulse beat is used as a permitting signal for gas pressure increase in the sleeve by the discrete value of pressure change, and when gas pressure in the sleeve reaches a value which is a multiple of the discrete value of pressure change the pumping is interrupted, and at the same time in the second mode the impulses of pulse are supplied;
    transmitting the impulses in the first mode and in the second mode by communicating means;
    receiving the thus formed and transmitted impulses by receiving means at a location spaced from a patient; and
    determining a lower blood pressure as a product of the number of impulses in the first mode by the discrete value of pressure change, a higher blood pressure as a product of the number of impulses in both modes by the discrete value of pressure change, and time intervals between pulse beats as time intervals between the impulses in the second mode.

* * * * *